US00PP25433P3

(12) United States Plant Patent
Swartz et al.

(10) Patent No.: US PP25,433 P3
(45) Date of Patent: Apr. 14, 2015

(54) BLACKBERRY PLANT NAMED 'BLACK JACK'

(50) Latin Name: ***Rubus* spp. L.**
Varietal Denomination: Black Jack

(71) Applicant: Five Aces Breeding LLC, Oakland, MD (US)

(72) Inventors: Harry J. Swartz, Oakland, MD (US); Peter Edward Vinson, Hernhill Faversham Kent (GB)

(73) Assignee: Five Aces Breeding LLC, Oakland, MD (US)

( * ) Notice: Subject to any disclaimer, the term of this patent is extended or adjusted under 35 U.S.C. 154(b) by 115 days.

(21) Appl. No.: 13/815,240

(22) Filed: Feb. 13, 2013

(65) Prior Publication Data

US 2014/0230110 P1 Aug. 14, 2014

(51) Int. Cl.
*A01H 5/00* (2006.01)

(52) U.S. Cl.
USPC ..... Plt./203

(58) Field of Classification Search
USPC ..... Plt./203
See application file for complete search history.

*Primary Examiner* — Susan McCormick Ewoldt
(74) *Attorney, Agent, or Firm* — Rosenberg, Klein & Lee

(57) ABSTRACT

The present invention is a new and distinct thornless blackberry cultivar named 'Black Jack', which is capable of producing large and firm fruit with high soluble solids. The cultivar is characterized by its thornlessness and its fruit attributes. It has the fruit morphology of other very large blackberries grown on thorny cultivars, namely uneven drupelets. It is, however, firmer than other large fruited types, and has very high soluble solids, up to 14%. 'Black Jack' plants are also unusual amongst the very large blackberry cultivars in that they produce commercial quantities of fruit, greater than 13 tons per acre on 2 year old potted plants.

6 Drawing Sheets

Figure 1:
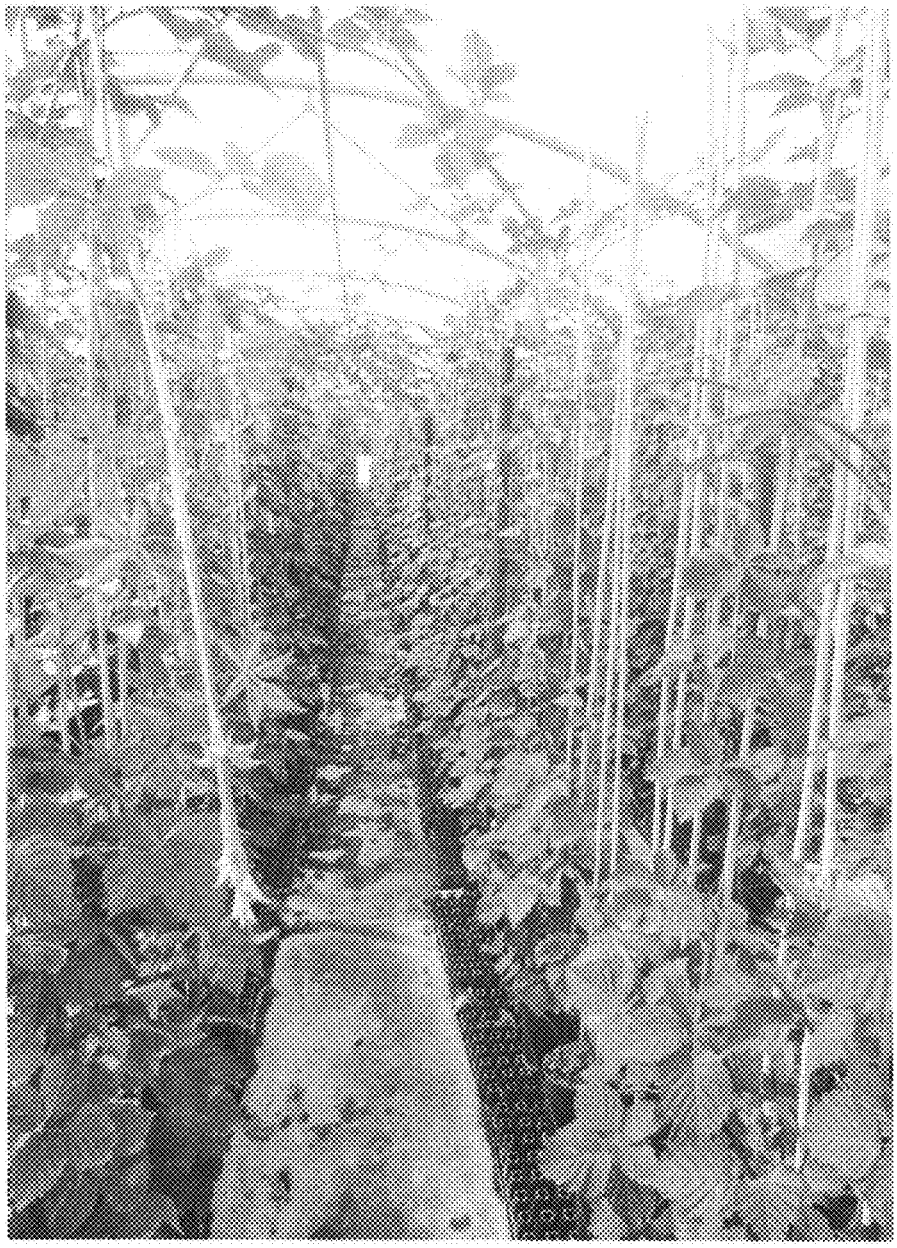

Title: 'Blackberry plant named 'Black Jack'.
Latin name: *Rubus* spp. L.
Varietal denomination: 'Black Jack'.

FIELD OF THE INVENTION

This invention concerns a new and distinct cultivar of thornless blackberry plant with a botanical name of *Rubus* spp. L. The new cultivar is distinguished from other cultivars by its combination of fruit firmness, sweetness and size, and plant productivity and thornlessness. 'Black Jack' is thereby suitable for premium fresh fruit marketing in commercial temperate zone production areas.

DESCRIPTION OF RELATED PRIOR ART

Several cultivars of blackberry plants are known. For instance, western U.S. cultivars with an origin of the *Rubus ursinus* L or *R. laciniatus*: 'Marion' (unpatented), 'Cascade' (unpatented), 'Siskiyou' (unpatented), 'Kotata' (unpatented) and 'Obsidian' (unpatented), and 'Onyx' (U.S. Plant Pat. No. 22,358) have thorns and are trailing. 'Thornless Evergreen' (unpatented) and its derivatives are trailing with deeply cut leaves. Of the upright or semi erect eastern blackberry cultivars with origins from *R. alleganiensis, R. cuniefolius* and possibly *R. argutus*: 'Kiowa' (U.S. Plant Pat. No. 9,861), 'Chickasaw' (U.S. Plant Pat. No. 11,861), 'Chesapeake' (U.S. Plant Pat. No. 13,878), and APF-8, -12, and -45 (U.S. Plant Pat. Nos. 15,788, 16,989 and 22,449, respectively), are thorny. Several eastern thornless semi erect blackberry cultivars exist including: 'Merton Thornless' (unpatented), 'Thornfree' (unpatented), 'Smoothstem' (unpatented), Dirksen Thornless' (unpatented), 'Chester Thornless' (unpatented), 'Hull Thornless' (unpatented), 'Loch Ness' (unpatented), 'Navaho' (U.S. Plant Pat. No. 6,679), and 'Nachez' (U.S. Plant Pat. No. 20,891). 'Black Jack' fruit are much larger and have much higher soluble solids and less acid taste than all of these cultivars. Other thornless blackberry cultivars with erect or semi erect plants and larger, lower acid, fruit are known to exist: 'Arapaho' (U.S. Plant Pat. No. 8,510), 'Apache' (U.S. Plant Pat. No. 11,865), 'Ouachita' (U.S. Plant Pat. No. 17,162) and 'Drisblacktwo' (U.S. Plant Pat. No. 22,002). Both 'Drisblacktwo' and 'Apache' are later ripening than 'Black Jack'. 'Arapaho' fruit has lower soluble solids and fruit weight. 'Ouachita' fruit is smaller size, and also exhibits a slight drupelet sterility not found in 'Black Jack'. All of the above cultivars do not exhibit the combination of fruit size, firmness and sweetness as 'Black Jack'. The new and distinct cultivar of the present invention is a blackberry plant named 'Black Jack'.

ORIGIN OF THE NEW CULTIVAR

The new cultivar of thornless blackberry originated from a controlled cross in glasshouse facilities in Oakland, Md. in Garrett Co., Md. The cross, designated: "PC", was 'Loch Ness' (unpatented) (female cultivar)×'Sweet Peter' (unpatented) (male cultivar) blackberries (*Rubus* L. subgenus *Rubus* including *R. allegheniensis* and *R. argutus*, the eastern upright blackberries). 'Loch Ness' was produced in Scottland and 'Sweet Peter' was a plant growing in a contract grower's field that was planted in 1992. 'Loch Ness' is a premium floricane fruiting blackberry cultivar with high yield but smaller, moderately firm, fruit. 'Loch Ness' primocanes are less vigorous and less upright than 'Black Jack' and 'Black Jack' flavor is less acidic and sweeter than 'Loch Ness.' It is adapted to cooler climates such as found in the United Kingdom. 'Sweet Peter' was selected as a parent for its low acidity and plant vigor. 'Sweet Peter' fruit is softer and smaller than 'Black Jack.' Similar to 'Loch Ness,' the general cane and plant features of 'Sweet Peter' are typical of eastern thornless blackberries and difficult to use to distinguish cultivars. In this claim, 'Black Jack' is claimed to be superior because of its superior fruit characteristics. Both crosses were genetically thornless with presumed parents originating from the cultivar 'Merton Thornless', an unpatented derivative of *R. ulmifolius* Schott. The cross was made in the winter of 2008 (such that the original plant is 6 years old) and was given the year designation "C"; thus the progeny designation was "CPC". CPC progeny seed from this cross was exported to the United Kingdom, germinated and grown in Kent United Kingdom. The present invention was first seedling of the CPC progeny selected in July 2010 and was therefore designated "-1VB" (selection one, Vinson Blackberry). Thus, the complete breeding designation of 'Black Jack' is "CPC-1VB".

SUMMARY OF THE NEW CULTIVAR

This application relates to a new and distinct large fruited, thornless, blackberry cultivar, botanically known as *Rubus* L. subgenus *Rubus*. The following characteristics are outstanding:

1. Production of fruit which is very firm and has low acid taste and high soluble solids.
2. Production of very large thick fruit, up to 4 cm in length, with a ratio of width to length averaging 4 units wide to 5 units long; or the diameter width is 80% as compared to the length of the fruit.
3. The season of production can exceed 6 weeks as long basal fruit trusses readily occur.
4. 'Black Jack' canes are vigorous, floricane-fruiting and completely thornless.

These characteristics make 'Black Jack' suitable as a mid-summer thornless blackberry for premium fresh fruit marketing in commercial production areas with at least 500 hours of chilling.

Overwintered 'Black Jack' plants with floricanes in southern Spain produced insufficient bud break after 250 chilling hours. In controlled chilling tests, 'Black Jack' floricanes had sufficient bud break after 500 hours chilling, similar to other moderate chilling blackberry cultivars such as Arapaho and Shawnee, but more than Choctaw and Kiowa (U.S. Plant Pat. Nos. 8,510, 5,686, 6,678, 9,861 respectively). Floricane fruit production has not been tested in areas that experience significant sub freezing temperatures, therefore, no claims are made concerning cold hardiness below −7° C.

The following characteristics are useful in distinguishing this cultivar from other cultivars and can be useful for cultivar identification. Plants used for these observations were grown in uncrowded conditions and in full sunlight.

1. Canes are completely thornless and semi upright after the first growing season.
2. Floricanes produce fruit which is very large, firm, does not bleed and is very high in soluble solids.
3. Fruit can be borne on normal apical and mid floricane trusses and long trusses arising from basal floricane buds which produce a later crop.
4. Fruit is relatively thick, with a diameter 80% of the length of the fruit.
5. Fruit is attractive, but exhibits some drupelets which are recessed producing an uneven fruit surface.

BRIEF DESCRIPTION OF THE PHOTOGRAPHS

The accompanying photographs show typical characteristics of the new variety:

FIG. 1. shows the vigor and growth habit of one year old tissue culture 'Black Jack' plants grown on single stakes in a tunnel in pots in the United Kingdom.

Figure 2:
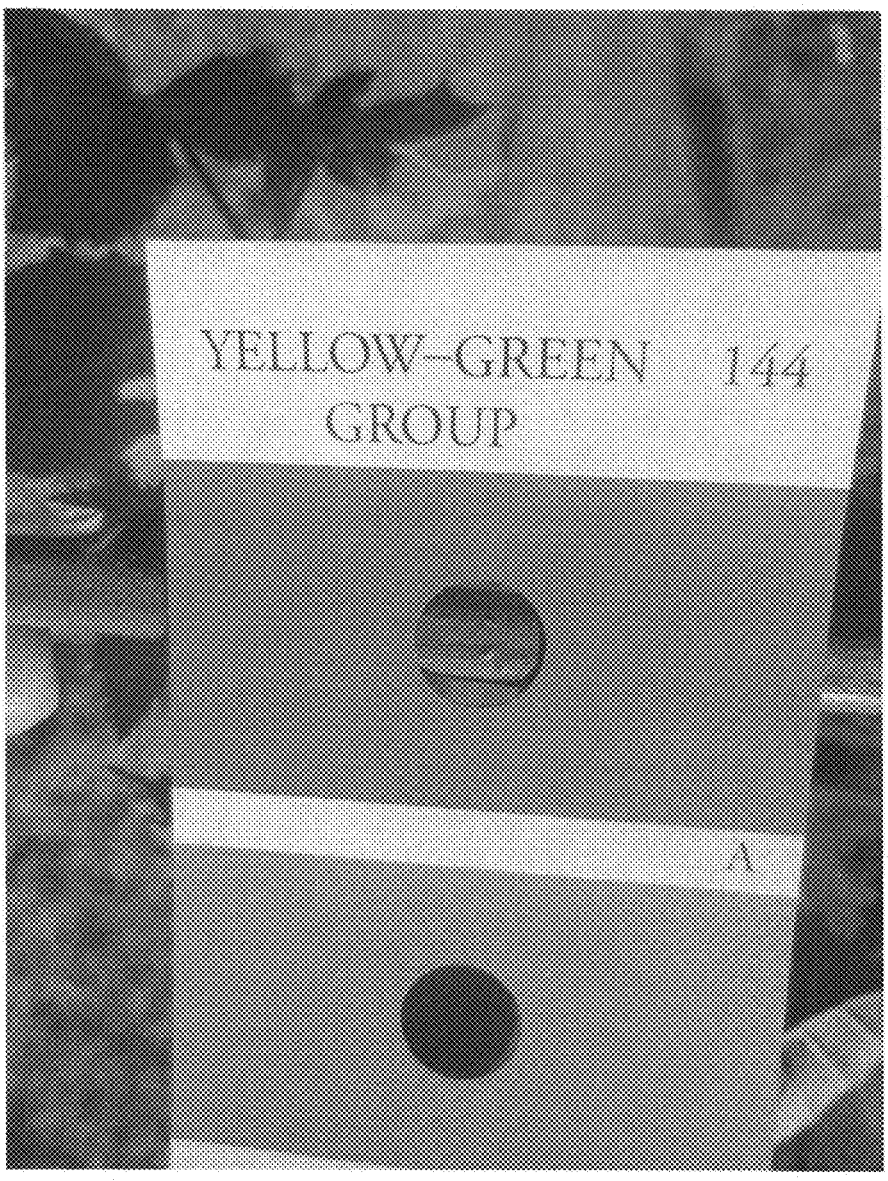

FIG. 2. shows the thornlessness of a 'Black Jack' primocane and 2001 Royal Horticulture Society Colour Plate 144.

Figure 3:
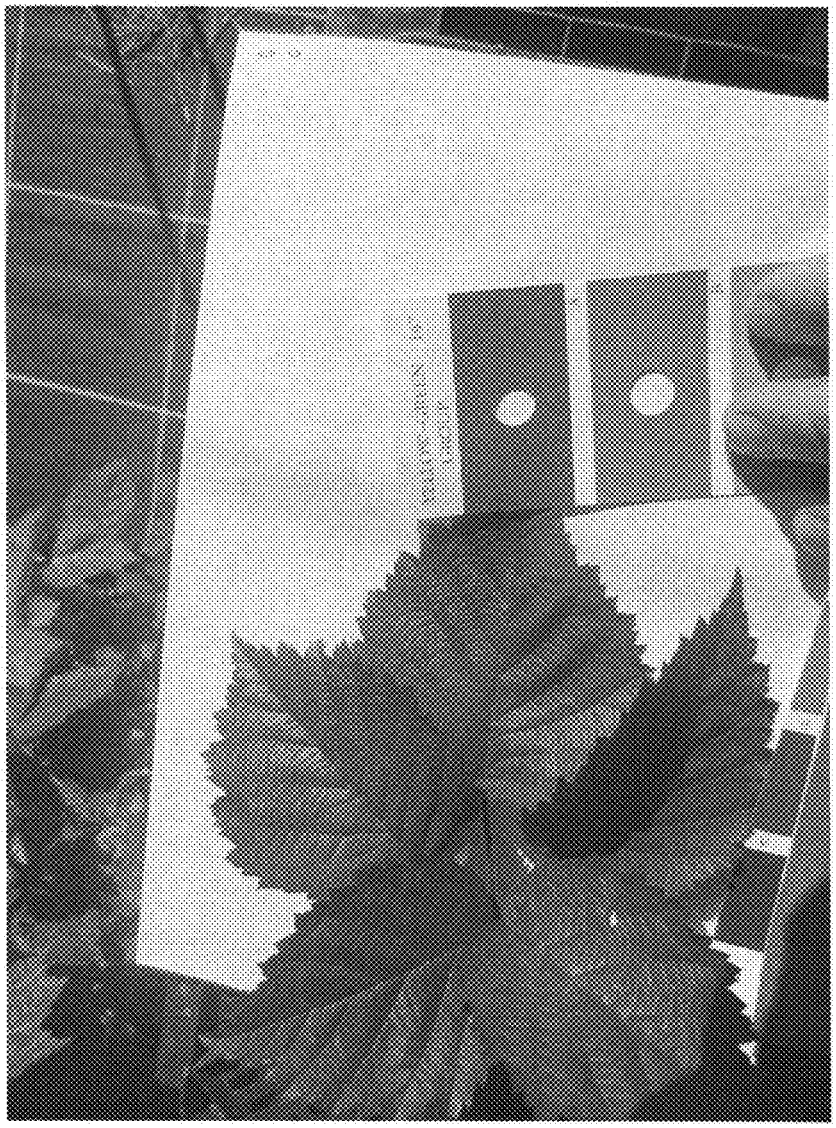

FIG. 3. shows the top surface of a 'Black Jack' leaf with 2001 Royal Horticultural Society Colour Plate 147 and the pattern of leaf attachment and leaf blade smoothness and venation.

Figure 4:
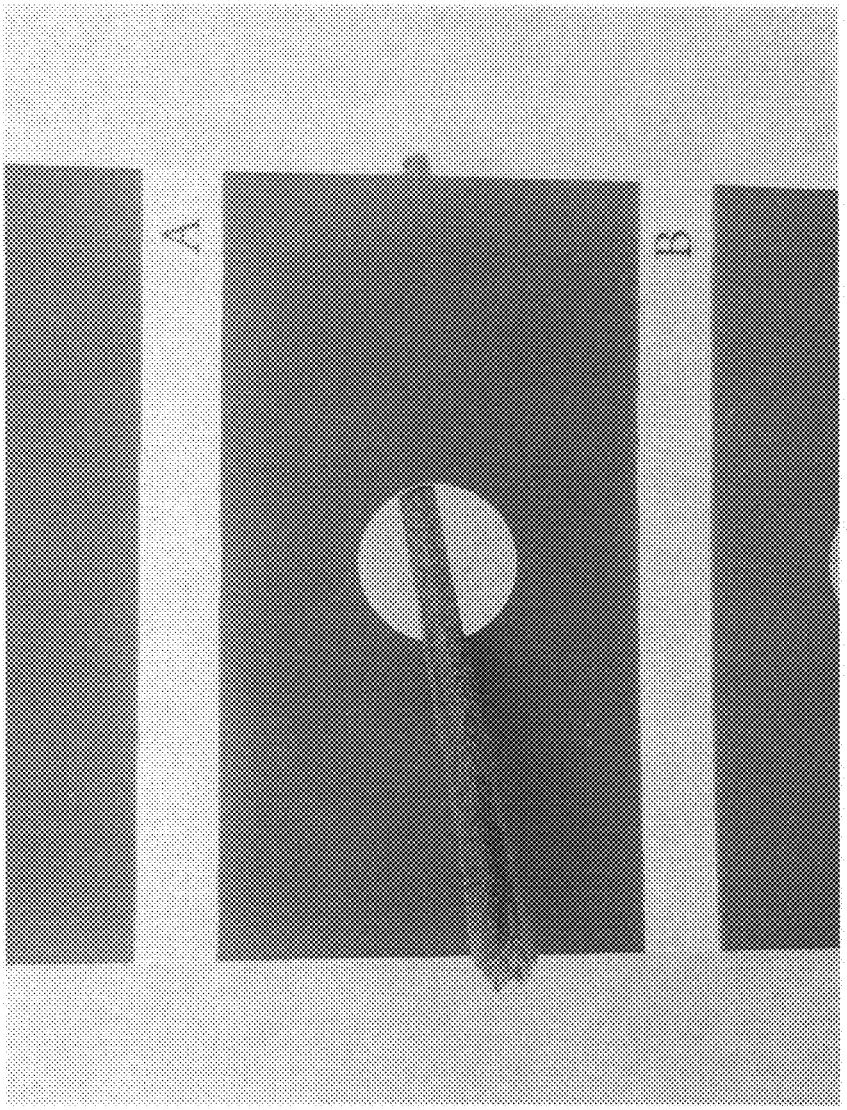

FIG. 4. shows the red blush on a thornless petiole from the leaf on a 'Black Jack' primocane with 2001 Royal Horticultural Society Colour Plate 184B.

Figure 5:
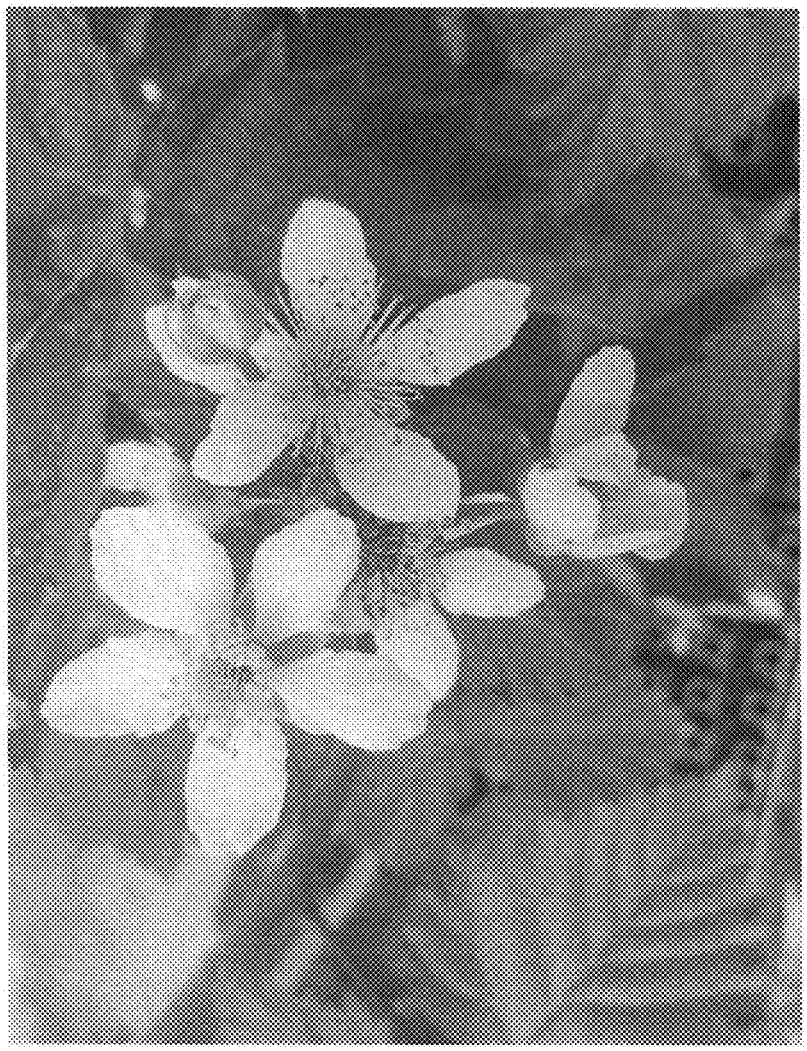

FIG. 5. shows a flower cluster of 'Black Jack' at various stages of opening.

Figure 6:
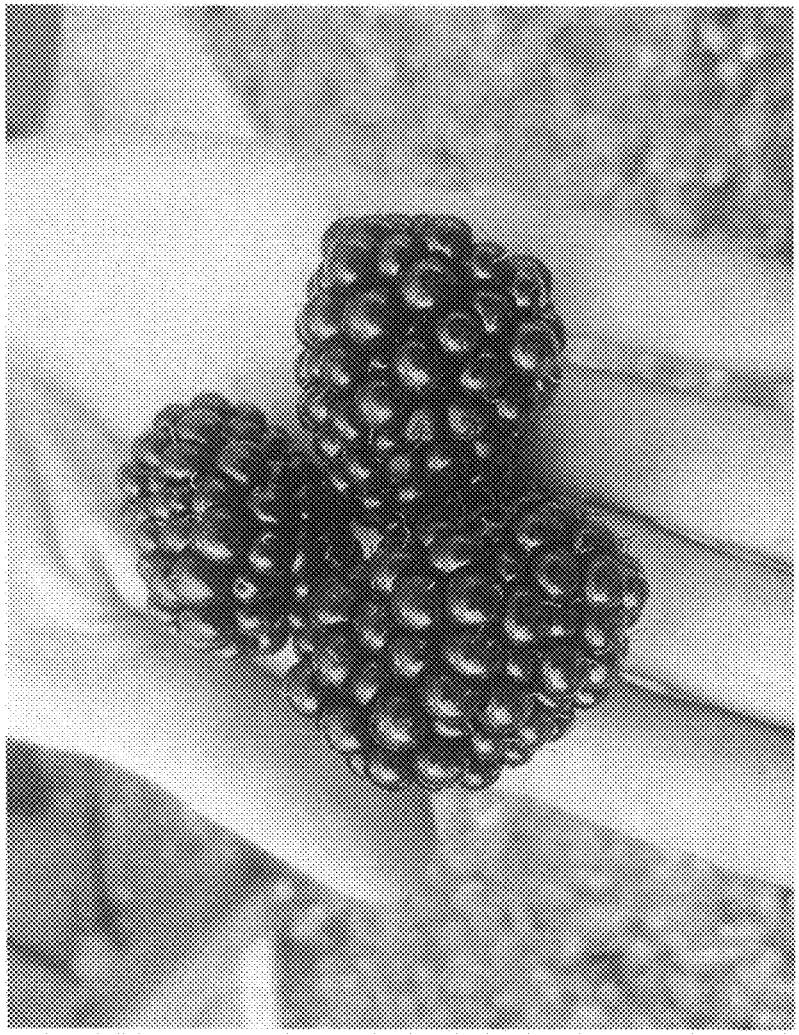

FIG. 6. shows 20 gram plus size 'Black Jack' fruit with persistant red blushed styles and uneven drupelet size.

DESCRIPTION OF THE NEW CULTIVAR

The following is a detailed description of 'Black Jack', the new cultivar, including fruit production, together with the cultivar's morphological characteristics. 'Black Jack' is a species hybrid, which contains a predominance of *Rubus* L subgenera *Rubus* blackberry traits found in its supposed eastern North American progenitor species, *Rubus allenganiensis* and *R. argutus*. It also exhibits several traits of its thornless parent species, *R. ulmifolius* Schott. It is therefore similar in leaf, cane and flower form to many of the other eastern semi-erect to erect thornless blackberry cultivars.

The description is based on information from plants grown in fields at Faversham, Kent, England and from plants grown in a greenhouse at Oakland, Md. As these climates differ, particularly in temperatures experienced in the growing season, we believe the description of 'Black Jack' will be consistent in other locations.

'Black Jack' produces vigorous primocanes which are trailing to semi erect in the first year after transplant (FIG. 1). After plant establishment in the first year, new primocanes are erect to semi-erect. Fall growth of primocanes can be "rat-tailed" and typical of the tip-layering response of most blackberries. 'Black Jack' produces a moderate number of root suckers (approximately 1.3 per plant) in second and subsequent years after transplant, typical of eastern thornless blackberry plants, but less than thorny cultivars. New primocanes are formed from the crown and average 4.1 per plant in the second year after field planting. During the growing season, canes are medium yellow-green colored (2001 Royal Horticultural Society Colour Plate No. 144A) with a red blush (2001 Royal Horticultural Society plate No. 184B) on less than 5% of the cane (FIG. 2). Canes on small plants can have much higher percentages of blush, especially when grown at lower nutrient levels in the field.

Vigorous canes usually branch, forming on average 3.4 branches when the canes branch. When growth averages 2 m per cane, branching will occur on 24% of the canes on young plants. On 2 year old potted plants, 50% of the canes are unbranched. This is less than expected for thorny eastern blackberry cultivars and typical of eastern thornless blackberry cultivars. Average total node number per cane is 42.4 for second year adult, non-tissue culture plants. Growth is moderately vigorous, reaching on average 278.8 cm in full sun. Internode length at 30 cm above ground in well lighted plants without floricanes is 6.3 cm. Cane diameter at the same location was 1.6 cm. 'Black Jack' nodes produce mostly single buds; when secondary buds occur, they are basal to the main bud and much reduced in size compared to the primary bud.

Thorns are completely absent (FIG. 2). Cane waxiness is slight, light rubbing will result in waxy reflection in the sun. Canes do not normally exfoliate or crack during the growing season. Canes have short silvery pubescence which is noticeable, but not downy.

The lower surface of 'Black Jack' leaves is pubescent gray-green resembling 2001 Royal Horticultural Society Colour Plate No. 137C. The upper leaf is dark green, most closely in hue to 2001 Royal Horticultural Society Colour Plate No. 147A (FIG. 3), depending on the amount of N fertilization and time of season. Senescing leaves have a green-yellow color resembling 2001 Royal Horticultural Society Colour Plate No 152A when senescence begins to occur after frost or in late October. Leaf abscission accelerates when temperatures less than −5° C. occur in fall. Petiole and petiolule color is similar to that of the primocane (2001 Royal Horticultural Society Colour Plate No.144A). Blush color on some canes and petioles can reach over 95% in the fall; the red color resembling in hue 2001 Royal Horticultural Society Colour Plate No.184B) (FIG. 4).

Vigorous plants have leaves that are 90% pentafoliolate in the lower 30 cm of the primocane. Above 30 cm, 95% of the leaves are pentafoliolate. The pentafoliolate terminal leaflet is, on average, 12.65 cm wide and 11.28 cm long. The trifoliolate terminal leaflet is, on average, 7.7 cm wide and 8.7 cm long. The pentafoliolate maximum leaf width, measured from apex of a lateral leaflet to the opposite lateral leaflet apex is, on average, 28.05 cm. The trifoliolate maximum leaf width, measured from apex of the lateral leaflet to the opposite lateral leaflet apex is, on average, 17.44 cm. Average lateral leaflet widths, at their widest point and on the largest lateral leaflet, were 6.4 cm and 6.2 cm for pentafoliolate and trifoliolate leaves, respectively. The pentafoliolate leaf petiole, basal petiolule and apical petiolule lengths averages 8.1 cm, 0.5 cm and 4.0 cm respectively for a total of 12.6 cm. Lateral leaflets are sessile and join at the petiole apex with the apical leaf petiolule (FIG. 3). This produces a palmate-pinnate pentifoliolate compound leaf. The trifoliolate leaf petiole and petiolule lengths averaged 4.2 cm and 2.3 cm respectively. Petiole widths are 0.38 cm and 0.22 cm for pentafoliolate and trifoliolate leaves respectively. Leaf serration is simple sawtooth; leaves have little laminar leaf puckering with a distinct depression directly above the midrib and secondary veins (FIG. 3). The venation pattern, a strong central vein with lateral subveins branching laterally and apically in both directions from the central leaflet axis and from non-opposite points along the main vein, is otherwise common for most cultivars of blackberry and cannot be used to distinguish this cultivar. Leaves have stipules at their petiole base, averaging 4 mm long and 0.3 wide.

'Black Jack' floricanes are similar to primocanes in color, resembling in hue 2001 Royal Horticultural Society Colour Plate No.144A (FIG. 2). Blush color on some canes and petioles can reach over 95% in the fall; the red color resembling in hue 2001 Royal Horticultural Society Colour Plate No.187A. The floricane epidermis cracks to a moderate amount and only at the cane base, with 1-5 cm long, 0.5 cm wide fissures running parallel with the cane. These fissures do not have exfoliating edges. The internal color of the fissures resembles 2001 Royal Horticultural Society Colour Plates 199B, 199C and 199D.

Flower trusses can appear at any floricane node from typical blackberry buds that are approximately 8 mm in length and 3 mm in maximum width by August and the color is similar to that of the primocane. Each cymose flower truss averages 12.2 nodes totaling 36.3 cm in length. Of these truss nodes, 6.6 have flowers on average; non-productive nodes are always at the flower truss base. The number of flowers per truss averages 9.0 in the apical part of the cane and 12.8 in the basal part of floricanes on 2 year old plants. For 3 year old plants, the numbers of flowers per truss is 8.7 on average over the whole cane.

Flower trusses average 4.77 monofoliolate leaves, 6.33 trifoliolate leaves and no pentafoliolate leaves. Monofoliolate leaves averaged 5.8 cm in length and 5.6 cm in width. Monofoliolate leaves had 2.6 cm long and 0.18 cm diameter petioles with 0.8 cm long, 0.2 cm wide stipules. On flower trusses, the terminal leaflet on trifoliolate leaves averaged 7.2 cm in length and was 5.9 cm in width. Width of trifoliolate leaves, from lateral leaflet to lateral leaflet, was 11.34 cm. The average maximum width of the largest lateral leaflet was 4.4 cm. The length of the petiolule was 1.4 cm and the petiole length was 3.5 cm with a diameter of 0.3 cm.

The unscented flower morphology and early fruit morphology is typical of most eastern thornless blackberry cultivars, having five pink (2001 Royal Horticultural Society Colour Plate No. 69A) petals that average 1.3 cm long and 0.8 cm wide (FIG. 5). Eventually these petals turn white (2001 Royal Horticultural Society Colour Plate No. 155D) and abscise days after pollination. Flowers have five 0.7 cm long, 0.48 cm wide at the base triangular gray-green and pubescent sepals (2001 Royal Horticultural Society Colour Plate No. 137C). The outer edge of the sepal is distinctly lighter colored than the center section due to an abundance of downy hairs producing a pair of minute framing stripes to the leaf-like appendage. Sepals are longer on primary fruits and always remain on the plant after fruit harvest. Flowers are borne on 3.2 cm long thornless peduncles which resemble in hue 2001 Royal Horticultural Society Colour Plate 144A. Peduncles on basal flower trusses are shorter, averaging 0.8 cm in length.

'Black Jack' flowers have on average 71.6 pistils on mid-season fruit and a similar number of anthers, 61.0. The anther stalk is light green-white (2001 Royal Horticultural Society Colour Plate 157C). Larger flowers average 158 pistils. The pistil style initially is green-white (2001 Royal Horticultural Society Colour Plate No. 157A) but at harvest, it becomes medium grayed-yellow (2001 Royal Horticultural Society Colour Plate No. 161A) with most developing a red blush (2001 Royal Horticultural Society Colour Plate No. 51C) on half the stylar stalk. The stylar stalk is persistent on ripe fruit and contrasts in color with the fruit flesh. The initial or primary fruit are easily distinguishable by long thick oval shape for this variety at 12 days post pollination. Fruit ripens from green (2001 Royal Horticultural Society Colour Plate No.144A) to blush red, to full red (2001 Royal Horticultural Society Colour Plate No. 184B and 184C) at immature and shiny then dull black (2001 Royal Horticultural Society Colour Plate No. 202A) at full ripe (FIG. 6).

Fruit weight averages 14.47 grams, ranging from 9.8 to 24.0 grams. Fruit length averages 3.3 cm long and 2.6 cm in diameter on apical flower trusses. Fruit is somewhat larger on basal long trusses averaging 3.9 cm long and 3.0 cm in diameter. Receptacle diameter at the abscission zone is on average 0.52 cm regardless of the fruit origin on the plant. As in all blackberries, the receptacle is carried along with the drupelets as a harvested ripe fruit. 'Black Jack' fruit are cohesive and firm and will not leak pigment in normal transport and storage. 'Black Jack' is low in acid by taste and high in soluble solids by refractometer, averaging 11.3% brix over the whole season with a range of 9 to 14% on 2 year old plants. 'Black Jack' drupelets are not uniformly distributed in size and presentation on the fruit; this produces a less than regular surface (FIG. 6). This characteristic is similar to other large fruited blackberries, for example the thorny cultivars, 'Kiowa' and 'Chesapeake', and is typical for 'Black Jack'.

Without tunnels, fruit is ripe beginning the last week in July in Kent, United Kingdom where the 5% ripe date in 2012 was July 27. Fruit harvest lasts until late August with the 95% ripe date of 20 Aug. 2012. This is early midseason and comparable to 'Loch Ness'.

FRUIT PRODUCTION

'Black Jack' has been tested in a potted plant trial in Kent. The following data were collected in the summer of 2012. Total floricane yield was 6.2 lbs per plant on 2 year old plants with 86% class 1 fruit and 3.5 lbs per plant on 1 year old plants with 77% class 1 fruit . 'Loch Ness', a very high yielding type for the United Kingdom, averaged 4.4 lbs per plant with 75% class 1 fruit. A yield of 6.2 lbs per plant is equivalent to 26,832 lbs per acre at 10 ft between rows.

'Black Jack' has been produced from tissue culture, by single node primocane cuttings and crown divisions for root suckers and tip layers, as is commonly used for thornless blackberry since 2010 in both Faversham, Kent, United Kingdom and Oakland, Md., U.S. Tissue culture propagation was achieved by dividing forced branches of in vitro stems or "plantlets." 'Black Jack' can be asexually propagated by tissue culture, tip layering or root suckers. No off-type plants have been observed in the history of asexual propagation of this cultivar by any method.

What is claimed:

1. A new and distinct thornless floricane-bearing blackberry plant known as 'Black Jack' as described herein, illustrated and identified by the characteristics set forth above.

* * * * *